(12) United States Patent
Jeong et al.

(10) Patent No.: US 7,919,278 B2
(45) Date of Patent: Apr. 5, 2011

(54) METHOD OF AMPLIFYING NUCLEIC ACID FROM A CELL USING A NONPLANAR SOLID SUBSTRATE

(75) Inventors: Sung-young Jeong, Yongin-si (KR); Kyu-youn Hwang, Yongin-si (KR); Joon-ho Kim, Yongin-si (KR); Jung-im Han, Yongin-si (KR); Hun-joo Lee, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 741 days.

(21) Appl. No.: 11/841,107

(22) Filed: Aug. 20, 2007

(65) Prior Publication Data

US 2008/0044864 A1   Feb. 21, 2008

(30) Foreign Application Priority Data

Aug. 21, 2006  (KR) .................. 10-2006-0079053
Aug. 21, 2006  (KR) .................. 10-2006-0079054
Aug. 21, 2006  (KR) .................. 10-2006-0079055
Aug. 21, 2006  (KR) .................. 10-2006-0079056

(51) Int. Cl.
    *C12P 19/34* (2006.01)
    *C12Q 1/68* (2006.01)

(52) U.S. Cl. .......................... 435/91.2; 435/6

(58) Field of Classification Search ............... None
    See application file for complete search history.

(56) References Cited

U.S. PATENT DOCUMENTS

| | | | |
|---|---|---|---|
| 5,085,779 A | 2/1992 | Crane et al. | |
| 5,234,809 A | 8/1993 | Boom et al. | |
| 5,705,628 A | 1/1998 | Hawkins | |
| 6,291,166 B1 | 9/2001 | Gerdes et al. | |
| 6,498,007 B1 | 12/2002 | Adachi et al. | |
| 6,617,105 B1 | 9/2003 | Rudi et al. | |
| 2002/0042125 A1 | 4/2002 | Petersen et al. | |
| 2004/0241462 A1 | 12/2004 | Lee et al. | |
| 2006/0234379 A1 | 10/2006 | Lim et al. | |
| 2006/0270031 A1 | 11/2006 | Hwang et al. | |
| 2007/0264675 A1 | 11/2007 | Toner et al. | |
| 2008/0044884 A1 | 2/2008 | Hwang et al. | |
| 2008/0044885 A1 | 2/2008 | Hwang et al. | |
| 2008/0070282 A1 | 3/2008 | Hwang et al. | |

FOREIGN PATENT DOCUMENTS

| | | |
|---|---|---|
| EP | 0208647 | 1/1987 |
| EP | 1712284 A1 | 10/2006 |
| EP | 1726641 A1 | 11/2006 |
| GB | 2152030 | 7/1985 |
| JP | 02-209814 A | 8/1990 |
| JP | 2001-098007 A | 4/2001 |
| JP | 2005-295969 A | 10/2005 |
| KR | 1020010032806 | 4/2001 |
| KR | 1020060068979 | 6/2006 |
| KR | 1020060109254 A | 10/2006 |
| WO | 9523872 A1 | 9/1995 |
| WO | 9851693 A1 | 11/1998 |
| WO | 9929703 A2 | 6/1999 |
| WO | 03010278 A2 | 2/2003 |
| WO | 2004087226 A1 | 10/2004 |
| WO | 2005093065 A1 | 10/2005 |

OTHER PUBLICATIONS

Deng et al. Detection of hepatitis A virus in environmental samples by antigen-capture PCR. Applied and Environmental Microbiology (1994) 60(6): 1927-1933.*
Friedland et al. Development of a polymerase chain reaction assay to detect the presence of *Streptococcus pneumoniae* DNA. Diagnostic Microbiology and Infectious Disease (1994) 20(4): 187-193.*
Cady et al. Nucleic acid purification using microfabricated silicon structures. Biosensors and Bioelectronics (2003) 19: 59-66.*
Tashiro, T. Antibacterial and bacterium adsorbing macromolecules. Macromolecular Materials and Engineering (2001) 286(2): 63-87.*
Eisenach et al. Pediatric blood culture evaluation of the Bactec Peds Plus and the DuPont Isolater 1.5 systems. Diagnostic Microbiology and Infectious Disease (1992) 15: 225-231.*
Rudolph et al. Evaluation of Polymerase Chain Reaction for Diagnosis of Pneumococcal Pneumonia. Journal of Clinical Microbiology (1993) 31(10): 2661-2666.*
Barbe, L., Mechanismes D'Adherences Des Leucocytes Aux Fibres Synthetiques. Application a La Filtration Du Sang, These pour obtenir le grade de docteur a L'Universite Paris 7, U.F.R. de physique, Dec. 14, 2001, pp. 1-197.
Wang, D. et al., Measurements of scattered light on a microchip flow cytometer with integrated polymer based optical elements, Lab Chip, 2004;4: pp. 372-377.
Ikada Y. et al, Surface modification of polymers for medical applications, Biomaterials 1994;15(10): pp. 725-736.
Absolom, D.R., et al.; "Surface Thermodynamics of Bacterial Adhesion"; Applied and Environmental Microbiology; vol. 46, No. 1; pp. 90-97; Jul. 1983.
Acarturk TO et al.., Control of attachment, morphology, and proliferation of skeletal myoblasts on silanized glass, Journal of Biomedical materials research, Mar. 15, 1999, vol. 44, No. 4, pp. 355-370.
Spargo BJ et al., Spatially controlled adhesion, spreading, and differentiation of endothelial cells on self-assembled molecular monolayers, Proceedings of the National Academy of Sciences, USA, vol. 91, Nov. 1994, pp. 11070-11074.
Liu Q Y et al., Synaptic connectivity in hippocampal neuronal networks cultured on micropatterned surfaces, . Developmental Brain Research Apr. 14, 2000, vol. 120, No. 2, Apr. 14, 2000 pp. 223-231.

(Continued)

*Primary Examiner* — Young J Kim
*Assistant Examiner* — Angela M Bertagna
(74) *Attorney, Agent, or Firm* — Cantor Colburn LLP

(57) ABSTRACT

Provided is a method of amplifying nucleic acid from a comprising: contacting a cell-containing sample with a nonplanar solid substrate in a liquid medium having a pH range of 3.0-6.0 to attach the cell to the solid substrate; washing the nonplanar solid substrate to remove materials that are not attached thereto; and performing PCR using the nucleic acid from the cell attached to the nonplanar solid substrate as a template sample to amplify nucleic acid from the cell, wherein the contacting, washing and PCR processes are performed in a single vessel.

12 Claims, 7 Drawing Sheets

OTHER PUBLICATIONS

Yang Changming et al., Electrically driven microseparation methods for pesticides and metabolites: III. Capillary electrochromatography with novel silica-based stationary phases having a surface-bound surfactant moiety, Electrophoresis, vol. 21, No. 10, Jun. 2000 pp. 1977-1984.

European Search Report dated Aug. 22, 2008 for Application No. 07114683.1-2405. (All References cited in Search report listed in this Information Disclosure Statement or in a previous Information Disclosure Statement).

Eng, Jan et al. "Effect of sodium polyanethol sulfonate in blood cultures", J Clin Microbiol. Feb. 1975; 1(2): 119-123.

Park et al., "Cylindrical pillars in silicon PCR chip enhance the performance of DNA amplification", Solid State Sensors, Actuators and Microsystems, 2005. Digest of Technical Papers. Transducers '05. The 13th International Conference, Seoul, KR, Jun. 5-9, 2005, Piscataway, NJ, IEEE, vol. 2, Jun. 5, 2005, 1604-1607.

Fredricks, et al., Improved Amplification of Microbial DNA from Blood Cultures by Removal of the PCR Inhibitor Sodium Polyanetholesulfonate, Journal of Clinical Microbiology, 1998, vol. 36 No. 10, pp. 2810-2816.

Hwang, K.Y. et al., Bacterial DNA Sample Preparation from Whole Blood Using Surface-Modified Si Pillar Arrays, Anal. Chem., 2008, vol. 80 (20), pp. 7786-7791.

Millar, et al., A simple and sensitive method to extract bacterial, yeast and fungal DNA from blood culture material, 2000, vol. 42, pp. 139-147, Journal of Microbiological Methods.

Panaro, N.J. et al., Micropillar array chip for integrated white blood cell isolation and PCR, Biomolecular Engineering, 2005, vol. 21, pp. 157-162.

Absolom, D. R. et al., Adhesion of hydrophilic particles (human erythrocytes) to polymer surfaces: Effect of pH and ionic strength, Colloids and Surfaces, vol. 21, 1986, 447-456.

Henriksson, A. et al., Characteristics of the adhesive determinants of *Lactobacillus fermentum* 104, Appl. Environ. Microbiol., 57(2); 1991, 499-502.

Herron, P. R. et al., New Method for Extraction of Streptomycete Spores from Soil and Application to the Study of Lysogeny in Sterile Amended and Nonsterile Soil, Appl. Environ Microbiol. 1990; 56(5): 1406-1412.

Saito, T. et al., Adherence of oral streptococci to an immobilized antimicrobial agent, Arch Oral Biol. Aug. 1997; vol. 42 (8): 539-45.

Ujam, L.B. et al., Cell separation by expanded bed adsorption: use of ion exchange chromatography for the separation of *E. coli* and *S. cerevisiae*, Bioprocess and Biosystems Engineering, vol. 23(3): 245-250, publication year = 2000.

\* cited by examiner

METHOD OF AMPLIFYING NUCLEIC ACID FROM A CELL USING A NONPLANAR SOLID SUBSTRATE

This application claims priority to Korean Patent Application Nos. 10-2006-0079053, 10-2006-0079054, 10-2006-0079055, and 10-2006-0079056, each filed on Aug. 21, 2006, and all the benefits accruing therefrom under 35 U.S.C. §119, the disclosure of each is incorporated herein in its entirety by reference.

BACKGROUND OF THE INVENTION

1. Field of the Invention

The present invention relates to a method of amplifying nucleic acid from a cell using a nonplanar solid substrate.

2. Description of the Related Art

In conventional methods of amplifying nucleic acids from a cell, cell separation, nucleic acid isolation and nucleic acid amplification are separately performed. Generally, cell separation is performed using centrifugal separation and filtration.

Conventional methods of purifying nucleic acids using a solid phase are known. For example, U.S. Pat. No. 5,234,809 discloses a method of purifying nucleic acids using a solid phase to which nucleic acids bind. However, this method is time-consuming and complicated, and thus is not suitable for implementation on a Lab-On-a-Chip (LOC). In addition, this method requires the use of a chaotropic substance. When a chaotropic salt material is not used in the method, the nucleic acids do not bind to the solid phase.

U.S. Pat. No. 6,291,166 discloses a method of archiving nucleic acids using a solid phase matrix. This method is advantageous in that nucleic acids are irreversibly bound to the solid phase matrix, allowing for delayed analysis or repeated analysis of the nucleic acid solid phase matrix complexes. However, in this method, the solid phase matrix has a positively charged surface (e.g., alumina), that must be rendered hydrophilic with basic materials, such as NaOH. Nucleic acids then irreversibly bind to the hydrophilic alumina, and thus cannot be separated from the alumina.

U.S. Pat. No. 5,705,628 discloses a method of reversibly and non-specifically binding DNA from a DNA-containing solution mixed with a salt and polyethylene glycol to a magnetic microparticle having a carboxyl group-coated surface. This method uses a magnetic microparticle having a carboxyl group-coated surface, a salt, and polyethylene glycol, in order to isolate DNA from the solution.

As described above, conventional methods of isolating and purifying a nucleic acid require addition of a high-concentration reagent for DNA binding. However, such addition can affect subsequent processes, such as a polymerase chain reaction (PCR), and therefore cannot be used on a lab-on-a-chip (LOC). In addition, conventional methods of isolating and purifying a nucleic acid are performed independently from a method of purifying or concentrating a cell. Furthermore, a method of performing isolation of a cell from a sample and amplification of nucleic acid from the cell in a single vessel is not known.

Accordingly, there is a need to develop a method of amplifying nucleic acid from a cell using a solid substrate in which a cell is isolated or concentrated by binding the cell to a solid surface, such as a substrate, and immediately thereafter, a nucleic acid derived from the cell can be isolated, purified and concentrated due to high affinity of the solid substrate for the nucleic acid.

In addition, in a conventional method of detecting a microorganism from blood, there are many cases where the concentration of the microorganism is so low that the microorganism cannot be directly detected. To solve this problem, a method of growing the microorganism by culturing the blood has been developed. In general, a medium including sodium polyanethol sulfonate (SPS) is used in blood culture (for example, Blood Culture Bottle (BC); Hy Laboratories Ltd. (Israel)). SPS is a polyanion anticoagulant used for survival of bacterial cells in blood culture. In particular, SPS is added to fluid blood culture media in many laboratories in order to counteract the bacterial inhibitors of fresh human blood. SPS has a structure similar to that of a nucleic acid base, and thus SPS acts as an intercalator which acts to inhibit any subsequent PCR performed on samples obtained from the blood sample. In addition, the SPS is not removed by commercially available nucleic acid isolation kits, such as, for example, a QIAGEN™ kit. Accordingly, for a successful PCR, the SPS has to be separately removed from any nucleic acid which has been isolated using a conventional nucleic acid isolation kit. If the SPS is not removed from a nucleic acid including SPS, for example, nucleic acid isolated from a blood culture including SPS, the sample has to be diluted more than about 5,000 times prior to amplifying the nucleic acid by performing PCR.

BRIEF SUMMARY OF THE INVENTION

The present invention provides a method of amplifying nucleic acids from a cell using a nonplanar solid substrate.

In an embodiment, the method comprises contacting a sample comprising a cell with a nonplanar solid substrate in a liquid medium having a pH in a range of 3.0-6.0 to attach the cell to the nonplanar solid substrate; washing the nonplanar solid substrate to remove materials that are not attached thereto; and performing a polymerase chain reaction (PCR) using the cell attached to the nonplanar solid substrate as a template sample to amplify nucleic acid from the cell, wherein the contacting, washing and performing PCR are performed in a single vessel.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
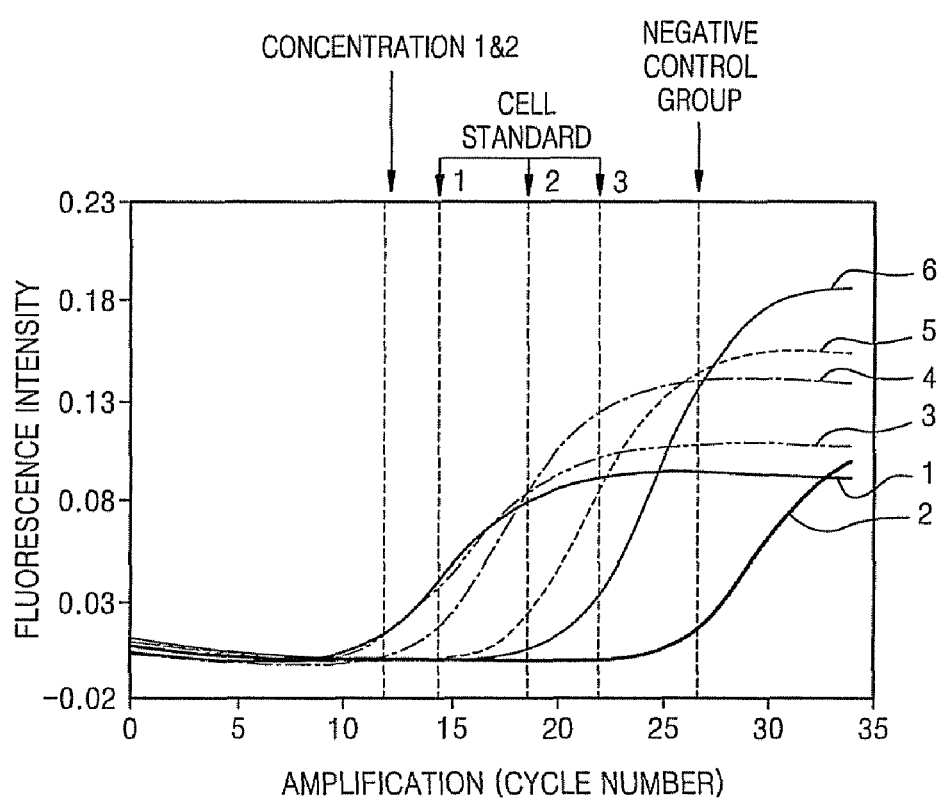
FIG. 1 is a graph showing results of PCR performed after attaching E. coli to a nonplanar solid substrate and then using DNA from the attached E. coli as a template for the PCR, according to an embodiment of the present invention.

The invention will now be described more fully hereinafter with reference to the accompanying drawings, in which embodiments of the invention are shown. The invention may, however, be embodied in different forms and should not be construed as limited to embodiments set forth herein. Rather these embodiments are provided so that this disclosure will be through and complete, and will fully convey the scope of the invention to those skilled in the art.

In one embodiment, the invention provides a method of amplifying nucleic acid from a cell. The method comprises contacting a sample comprising a cell with a nonplanar solid substrate in a liquid medium having a pH in a range of 3.0-6.0 to attach the cell to the nonplanar solid substrate; washing the nonplanar solid substrate to remove materials that are not attached thereto; and performing a polymerase chain reaction (PCR) using the cell attached to the nonplanar solid substrate as a template sample to amplify nucleic acid from the cell, wherein the contacting, washing and performing PCR are performed in a single vessel.

As used herein, the term "cell" means a prokaryotic or eukaryotic cell, a plant cell, a bacteria cell, a pathogenic cell, a yeast cell, an aggregate of cells, a virus, a fungus, or other nucleic acid containing biological material, such as, for example, an organelle.

As used herein, the term "nucleic acid" means DNA, RNA or PNA, or a combination thereof, preferably, DNA. The DNA, RNA, or PNA can be in any possible configuration, i.e., in the form of double-stranded (ds) nucleic acid, or in the form of single-stranded (ss) nucleic acid, or as a combination thereof (in part ds or ss).

As used herein, the term "cell-binding" means the ability to bind a cell or other biomaterial, such as, for example a nucleic acid.

In a liquid medium containing a solid substrate, a cell such as, for example, a bacterial cell, can exist in the liquid medium or can be attached (i.e., bound) to the solid substrate. It is known that such a distribution of the cell is determined by the difference between the surface tension of the liquid medium and the surface tension of the cell. That is, when the surface tension of the liquid medium is greater than the surface tension of the cell, the cell can be easily attached to a solid substrate having a low surface tension, that is, a hydrophobic solid substrate. When the surface tension of the cell is greater than the surface tension of the liquid medium, the cell can be easily attached to a solid substrate having a high surface tension, that is, a hydrophilic solid substrate. When the surface tension of the microorganism is the same as the surface tension of the liquid medium, it is reported that surface tension does not affect attachment of cells to a solid substrate, and other interactions such as an electrostatic interaction affect attachment of cell to a solid substrate (Applied and Environmental Microbiology, July 1983, p. 90-97). In addition, it is known that the cell can be attached to the surface of the solid substrate by electrostatic attractive forces in addition to being thermodynamically driven by differences in the surface tension. However, the deposition speed of the cell on the solid substrate is very slow for attachment based on electrostatic attractive forces.

Therefore, in order to address these problems, the inventors of the present invention found that a large amount of cells can be separated by contacting a cell-containing sample with a nonplanar solid substrate in a liquid medium having a pH range of 3.0-6.0. The use of a nonplanar solid substrate provides increased the surface area upon which the cells bind, relative to a planar surface. Therefore, without being held to theory, it is believed that a large number of cells can be isolated by contacting a nonplanar solid substrate with a cell-containing sample in a liquid medium having a pH of 3.0 to 6.0 because the surface area of a nonplanar solid substrate is increased, relative to a planar substrate. Furthermore, by using a liquid medium of pH 3.0 to 6.0, the cell membrane of a cell can be denatured or disrupted and thus the cell is less soluble with respect to the solution and therefore relatively more cells can be bound to the surface of the nonplanar solid substrate. However, the present invention is not limited to such a mechanism.

In one embodiment, during the contacting process, the sample can be any sample containing a cell. For example, the sample can be a biological sample containing a cell, a clinical sample containing a cell or a lab sample containing a cell.

As used herein, the term "biological sample" means a sample that includes or is formed of a cell or tissue, such as a cell or biological liquid isolated from an animal or plant. The animal can be a human, preferably an individual human. The biological sample can be saliva, sputum, blood, blood culture, blood cells (for example, red blood cells or white blood cells), amniotic fluid, serum, sperm, bone marrow, tissue or micro needle biopsy sample, urine, peritoneum fluid, pleura fluid, or cell cultures. In addition, the biological sample can be a tissue section, such as a frozen section taken for a histological object. Preferably, the biological sample is a clinical sample derived from a human patient. More preferably, the biological sample is blood, blood culture, urine, saliva, or sputum. The biological sample can be a biological sample including sodium polyanethol sulfonate (SPS), for example, a blood culture including SPS.

Furthermore, the term "biological sample" means a sample that is formed comprising an organism, group of organisms from the same or different species, cells or tissues, obtained from the environment, such as from a body of water, from the soil, or from a food source or an industrial source.

SPS is a polyanion anticoagulant used for survival of bacteria cells in blood culture. In particular, SPS is added to fluid blood culture media in many laboratories in order to counteract the bacterial inhibitors of fresh human blood. SPS has a structure similar to that of nucleic acid base, and thus SPS acts as an intercalator, which may inhibit subsequent PCR performed on samples containing SPS. In addition, the SPS cannot be removed by conventional nucleic acid isolation kits, such as, for example, a QIAGEN™ kit, which is commercially available.

According to one embodiment of the present invention, a cell that is to be isolated can be a bacterial cell, fungus, or a virus.

According to one embodiment, in the contacting process, the biological sample can be diluted with a solution or buffer that can buffer the cell with a low pH. The buffer can be, for example, a phosphate buffer, such as sodium phosphate having a pH of 3.0 to 6.0, or an acetate buffer, such as sodium acetate having a pH of 3.0 to 6.0. The degree of dilution is not limited, and, for example, the biological sample can be diluted in a range of 1:1 to 1:1,000, and preferably, 1:1 to 1:10.

According to another embodiment, in the contacting process, the biological sample can have a salt concentration of 10-500 mM, and preferably, 50-300 mM. That is, the biological sample may have an acetate or phosphate ion concentration of 10-500 mM, preferably 50-300 mM.

In one embodiment, during the contacting process, the solid substrate contacted with the cell-containing sample can have a nonplanar shape so that the surface area of the solid substrate can be increased compared to a planar substrate. For example, the nonplanar solid substrate may have a corrugated surface. As used herein, the term "corrugated surface" denotes a non-level surface having grooves and ridges. The corrugated surface can be a surface with a plurality of pillars or a sieve-shaped surface with a plurality of pores. However, the corrugated surface is not limited thereto and may comprise other shapes.

In one embodiment, the nonplanar solid substrate can have various shapes. For example, the nonplanar solid substrate can be a solid substrate comprising a surface with a plurality of pillars, a bead-shaped solid substrate, or a sieve-shaped solid substrate having a plurality of pores in its surface. The solid substrate can be a single solid substrate or a combination of one or more solid substrates, such as a solid substrate assembly which fills a tube or container.

In one embodiment, in the contacting process, the nonplanar solid substrate can form an inner wall of a microchannel or microchamber of a microfluidic device. Accordingly, the method of amplifying nucleic acid from a cell according to the current embodiment can be used in a fluidic device or microfluidic device having at least one inlet and outlet in fluid communication with a channel or microchannel.

As used herein, the term "microfluidic device" incorporates the concept of a microfluidic device that comprises microfluidic elements such as, e.g., microfluidic channels (also called microchannels or microscale channels). As used herein, the term "microfluidic" refers to a device component, e.g., chamber, channel, reservoir, or the like, that includes at lest one cross-sectional dimension, such as depth, width, length, diameter, etc. of from about 0.1 micrometer to about 1000 micrometer. Thus, the term "microchamber" and "microchannel" refer to a channel and a chamber that includes at lest one cross-sectional dimension, such as depth, width, and diameter of from about 0.1 micrometer to about 1000 micrometer, respectively.

According to the current embodiment, in the contacting process, the nonplanar solid substrate used in the contacting step can have a surface having a plurality of pillars. Methods of forming pillars on a solid substrate are well known in the art. For example, micro pillars can be formed in a high density structure using a photolithography process used in a semiconductor manufacturing process. The micro pillars can have an aspect ratio of 1:1 to 20:1. However, the aspect ratio of the micro pillars is not limited thereto. As used herein, the term "aspect ratio" denotes a ratio of the cross-sectional diameter to the height of a pillar. In the pillar structure, the ratio of the height of the pillars to a distance between adjacent pillars may be in the range of 1:1 to 25:1. The distance between adjacent pillars may be in the range of 5-100 μm.

In one embodiment, in the contacting process, the nonplanar solid substrate can be hydrophobic and have a water contact angle of 70° to 95°. The hydrophobic property of the nonplanar solid substrate having a water contact angle of 70° to 95° can be obtained by coating octadecyldimethyl(3-trimethoxysilyl propyl)ammonium (OTC) or tridecafluorotetrahydrooctyltrimethoxysilane (DFS) on the nonplanar solid substrate. More specifically, the nonplanar solid substrate having a water contact angle of 70° to 95° can be obtained by self-assembled molecule (SAM) coating octadecyldimethyl (3-trimethoxysilyl propyl)ammonium (OTC) or tridecafluorotetrahydrooctyltrimethoxysilane (DFS) on a $SiO_2$ layer of the nonplanar solid substrate.

In this application, the term "water contact angle" refers to water contact angle measured by a Kruss Drop Shape Analysis System type DSA 10 Mk2. A droplet of 1.5 μl deionized water is automatically placed on the sample. The droplet was monitored every 0.2 seconds for a period of 10 seconds by a CCD-camera and analyzed by Drop Shape Analysis software (DSA version 1.7, Kruss). The complete profile of the droplet was fitted by the tangent method to a general conic section equation. The angles were determined both at the right and left side. An average value is calculated for each drop and a total of five drops per sample are measured. The average of the five drops is taken the contact angle.

According to one embodiment, in the contacting process, the nonplanar solid substrate can have at least one amine-based functional group at its surface. The surface of the nonplanar solid substrate having at least one amine-based functional group may be prepared by coating the nonplanar solid substrate with polyethyleneiminetrimethoxysilane (PEIM). For example, the coated surface can be obtained by self-assembled molecule (SAM) coating polyethyleneiminetrimethoxysilane (PEIM) on a $SiO_2$ layer of the nonplanar solid substrate. The amine-based functional group is positively charged in a range of pH 3.0 to 6.0.

According to another embodiment, in the contacting process, the nonplanar solid substrate can be a substrate formed of any kind of material that has the water contact angle described above, or has at least one amine-based functional group at its surface. For example, the nonplanar solid substrate can be formed of glass, silicon wafer, plastic, or the like, but is not limited thereto. When a nonplanar solid substrate with a surface having a water contact angle of 70° to 95° or a surface having at least one amine-based functional group is contacted with a sample containing a microorganism cell, the microorganism cell is assumed to be bound to the nonplanar solid substrate. However, the present invention is not limited to such a specific mechanism.

According to the current embodiment, the method of amplifying nucleic acid from a cell may further comprise, after the contacting process, washing the cells bound to the nonplanar solid substrate by introducing a washing solution to the nonplanar solid substrate to remove other materials, excluding the target cell, which are not bound to the nonplanar solid substrate. In the washing process, any solution that does not liberate the target microorganism cell bound to the nonplanar solid substrate from the nonplanar solid substrate and does remove impurities which may adversely affect subsequent processes can be used. For example, the washing solution can be an acetate buffer or phosphate buffer which is used as a binding buffer can be used as the washing solution. The washing solution may have a pH of 3.0 to 6.0.

In another embodiment, the method of amplifying nucleic acid from a cell further comprises amplifying nucleic acid from the cell attached to the nonplanar solid substrate by performing PCR.

In the nucleic acid amplification process, nucleic acid can be amplified by arbitrary methods known to those of ordinary skill in the art, preferably PCR. The term "PCR" denotes a polymerase chain reaction. More specifically, PCR is a method of amplifying target nucleic acid from a sample using a pair of primers that are specifically bound to the target nucleic acid with the use of a nucleic acid polymerase. In general, PCR requires several components, inducing a template, primer(s), nucleic acid polymerase, four types of nucleic acid monomers, such as, for example the DNA monomers dATP, dGTP, dCTP and dTTP, and buffer. In the nucleic acid amplification process, the DNA template may be nucleic acid that is exposed from the cell attached to the nonplanar solid substrate by thermal cycling during PCR. Thus, during the PCR process, for example, target nucleic acid can be amplified by adding reaction compositions of PCR, excluding the nucleic acid template, to a vessel containing the nonplanar solid substrate having the cell attached thereto and performing PCR. It is believed that that cells are disrupted during the thermocycling of the PCR during the pre-denaturation and/or denaturation process. However, the present invention is not limited to such specific mechanisms. Therefore, in the nucleic acid amplification process, a nucleic acid template derived from the cell attached to the nonplanar solid substrate, is used as the template nucleic acid in the PCR process without separately being isolated.

According to the current embodiment, the contacting, washing and amplification processes of the method of amplifying nucleic acid from a microorganism are performed in a single vessel. The vessel can be, for example, a microchannel, a microchamber, a tube and the like, but is not limited thereto. Preferably, the vessel can be a microchamber installed in a microfluidic device, and may include a PCR device. The PCR device can be, for example, a heater, a cooler and a thermostat. Therefore, in the method of amplifying nucleic acid from a microorganism according to the current embodiment of the present invention, the nucleic acid extraction and the nucleic acid amplification may be performed in the same microchamber.

The present invention will now be described in further detail with reference to the following examples. These examples are for illustrative purposes only and are not intended to limit the scope of the present invention.

EXAMPLES

Example 1

Separation of *E. coli* Cells from Blood, Disruption of the *E. coli* Cells and Nucleic Acid Amplification, Using a Nonplanar Solid Substrate Having a Pillar Structure In this example, a sample including cells was flowed into a fluidic device including an inlet and outlet, and having a chamber including a nonplanar solid substrate having a pillar array formed on a chip having an area of 10 mm×23 mm. Then, PCR was performed using DNA from cells bound to the nonplanar solid substrate as a template.

In the pillar array, the distance between pillars was 15 μm, the pillars had a height of 100 μm, and each of the pillars had a square-shaped cross-section, wherein each side of the square-shaped cross-section had a length of 25 μm. The surface of the nonplanar solid substrate having the pillar array formed thereon was formed of a $SiO_2$ layer.

A cell sample having a pH of 4.7, obtained by mixing blood including *E. coli* ($OD_{600}$=0.1) at a concentration of about $10^8$ cells/ml with an equal amount of an acetate buffer having a pH of 3.0, was used as the sample including cells.

The sample was pumped through the inlet of the fluidic device, through the chamber of the fluidic device and then out from the outlet of the fluidic device. 500 μl of the sample was pumped through the fluidic device at a flow rate of 200 μl/minute. Then the fluidic device was subjected to centrifugation to remove any sample solution remaining in the chamber, and subsequently 3.0 μl of a PCR reaction solution was added to the chamber.

A 3 μL PCR reaction solution was prepared to have the following components: 1×PCR buffer (Solgent Co. Ltd., Korea), 200 μM of each dNTP, 200 nM of each primer, 2.5 mM $MgCl_2$, 1 mg/mL BSA, 5% polyethylene glycol (PEG), 0.5×SYBR™ green, and a total of 0.3 units of Taq™ polymerase. The primers used had a nucleotide sequence of SEQ ID Nos:1 (tgtatgaaga aggcttcg) and 2 (aaaggtatta actttactc), respectively.

The fluidic device including the chamber was installed in a TMC-1000 PCR instrument (manufactured by Samsung Techwin, Co., Ltd., Korea) so that PCR could be performed in the fluidic device. Then, *E. coli* cells present in the fluidic device were disrupted by heat. In particular, the cells were disrupted by heating the sample at 95° C. for 10 seconds and then at 65° C. for 10 seconds; three heating cycles were performed.

After the cells were disrupted as described above, thermal cycling for PCR was performed. Conditions of the thermal cycling were as follows: predenaturation at 94° C. for 10 seconds, then denaturation at 94° C. for 10 seconds, annealing at 62° C. for 10 seconds and extension at 72° C. for 10 seconds. The denaturation, annealing and extension cycle was repeated 40 times.

The concentration of nucleic acid amplified during the PCR process was detected by SYBR™ green. FIG. 1 is a graph showing results of PCR performed according to the current example. Amplification is monitored by fluorescence intensity as a function of amplification cycle. The threshold cycle (Ct) is the cycle number in the PCR at which the reporter dye emission intensity rises above background noise. The Ct is inversely proportional to the copy number of the target template; the higher the template concentration, the lower the threshold cycle measured. Referring to FIG. 1, the graph shows Ct values (vertical lines) for various samples. In particular, FIG. 1 shows results obtained from a PCR performed after a sample having $10^7$ *E. coli* cells/ml were concentrated by attaching the cells to the nonplanar solid substrate, and then disrupted by heat to expose DNA from the disrupted cells for use as the PCR template. That is, in FIG. 1, curves 1 and 3 refer to a realtime PCR products curves for the samples 1 and 2 which is concentrated as mentioned above and the concentration Ct lines 1 and 2 refer to Ct lines for the curves 1 and 3. Curves 1 and 3 refer to 2 time repeats experiments under the same conditions. FIG. 1 demonstrates that the Ct values obtained in PCR using DNA from *E. coli* cells concentrated by attaching the cells to a nonplanar solid substrate, and then disrupted by heat were lower than Ct values obtained in PCR performed using the same process described above for a sample in which concentration of the *E. coli* cells by binding with a solid substrate did not occur (cell standard). In FIG. 1, curves 4-6 refer to a realtime PCR products curves for the standard samples 1-3 and the cell standard Ct lines 4-6 refer to Ct lines for the curves 4-6, respectively. The standard samples 1-3 refer to $10^7$ E. coli cells/reaction, $10^6$ E. coli cells/reaction, and $10^5$ E. coli cells/reaction. Curve 2 refers to a realtime PCR products curve for the negative sample, which does not contain any target DNA in PCR solution and the negative control group Ct line refers to Ct line for the curve 2. Therefore, FIG. 1 demonstrates that the E. coli cells were effectively concentrated using the nonplanar solid substrate, allowing for efficient PCR amplification of the target nucleic acid.

Example 2

Separation of E. coli Cells from Blood and Serum, and Nucleic Acid Amplification from the E. coli Cells, Using Nonplanar Solid Substrate Having a Pillar Structure: Effect of Washing For this example, a blood and serum sample including E. coli cells was pumped through a fluidic device as described in Example 1 to attach the cells to the nonplanar solid substrate. The effect of a washing step to remove materials that were not attached to the nonplanar solid substrate on PCR performed using DNA from the cells attached to the nonplanar solid substrate as a template was examined.

The pillar array was as described in Example 1.

Samples having a pH of 4.7, obtained by mixing either blood or serum including E. coli ($OD_{600}$=0.1) having a concentration of about $10^8$ cells/ml with an equal amount of an acetate buffer having a pH of 3.0, were used as the blood and serum samples including cells.

A volume of 500 µl of the blood and serum samples were pumped through the fluidic device at a flow rate of 200 µl/minute. If a washing process was performed, an acetate buffer having a pH of 4.0 was subsequently pumped through the fluidic device at the same flow rate. Then the fluidic device was centrifuged to remove any solution remaining in the chamber, and 3.0 µl of a PCR reaction solution was added to the chamber.

The 3.0 µl PCR reaction solution as described in Example 1 was used. The primers used in PCR had a nucleotide sequence of SEQ ID Nos: 1 and 2, respectively.

The fluidic device including the chamber was installed in a TMC-1000 (manufactured by Samsung Techwin, Co., Ltd., Korea) to permit performance of PCR in the fluidic device. Then, E. coli cells were disrupted by heating as described in Example 1.

After the cells were disrupted, thermal cycling for PCR was performed. Conditions of the thermal cycling were as described in Example 1.

The concentration of nucleic acid amplified during the PCR process was detected using SYBR™ green. FIGS. 2A and 2B are graphs showing the results of PCR performed according to the current example using DNA from disrupted E. coli cells obtained from a blood (FIG. 2A) or serum (FIG. 2B) sample that attached to the solid substrate.

Figure 2:
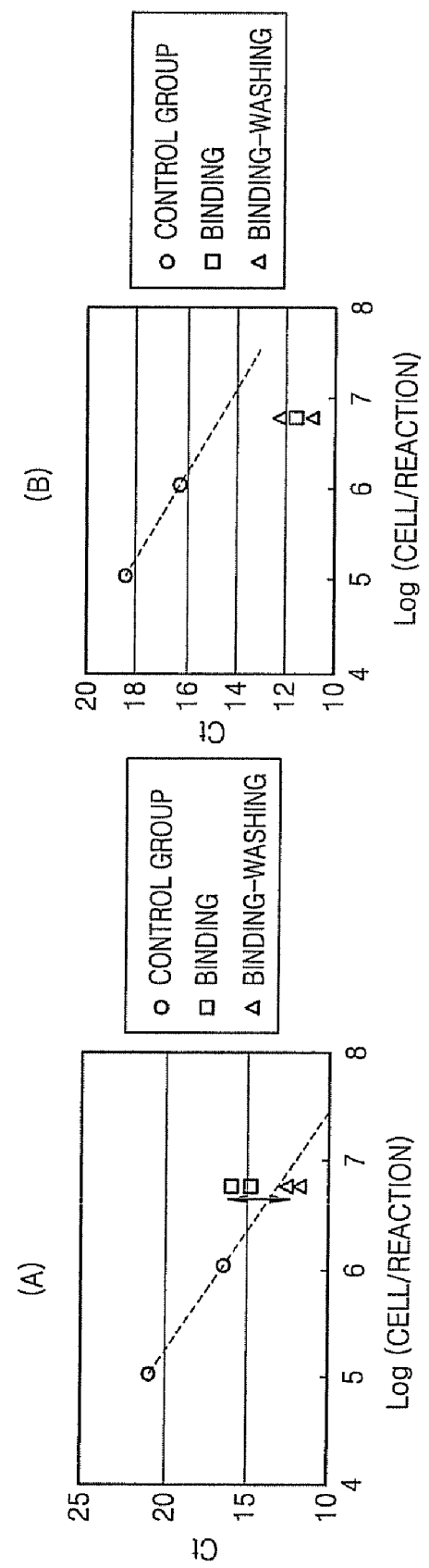
FIGS. 2A and 2B are graphs showing results of PCR performed after E. coli in a blood or serum sample was attached to a nonplanar solid substrate, and the cells were disrupted by heat prior to PCR, according to an embodiment of the present invention, wherein the PCR results are represented as Ct values.

The "control group" measurements shown in FIG. 2 represent PCR performed in the same way as described above on DNA prepared by isolating DNA from blood using a QiAamp DNA mini kit. The "binding" measurements in FIG. 2 represent PCR on a sample in which a washing process was not performed after the binding process, while the measurements denoted by "binding-washing" in FIG. 2 represent PCR on a sample in which the washing process was performed after the binding process. In FIG. 2A, an arrow represents Ct values reduced according to washing.

Referring to FIG. 2B (serum samples), Ct values of PCR performed using DNA from concentrated and disrupted E. coli cells with or without the washing step were lower than the extrapolated Ct values of PCR using DNA isolated from cells using the commercial purification kit. For the serum samples washing had negligible effect on the Ct observed. As illustrated in FIG. 2A, in the case of the blood samples, Ct values of PCR performed using DNA from concentrated and disrupted E. coli cells after the washing step were lower than the Ct values of PCR using DNA from concentrated and disrupted E. coli cells with no washing step. As a result, it can be inferred that a PCR inhibitor existed in the blood samples, and the PCR inhibitor was removed by the washing process. In FIG. 2, the cell concentration for the "binding" group and "binding washing" group at x axis refers to the initial cell concentration prior to subsequent cell concentration process.

Example 3

Separation of E. coli Cells from Blood, Disruption and Nucleic Acid Amplification from the E. coli Cells, Using Nonplanar Solid Substrate Having a Pillar Structure: Impact on the Concentration of E. coli Cells For this sample a blood sample including E. coli cells was pumped through a fluidic device as described in Example 1 to attach the cells to the nonplanar solid substrate. Then, the nonplanar solid substrate was washed to remove materials that were not attached thereto. Thereafter, the cells attached to the nonplanar solid substrate were disrupted by heat to obtain a cell lysate, and PCR was performed using DNA from the cell lysate as a template.

The pillar array was as described in Example 1.

Samples having a pH of 4.7 were obtained by mixing blood including E. coli ($OD_{600}$=0.01) having a concentration of about $10^7$ cells/ml or blood including E. coli ($OD_{600}$=0.001) having a concentration of about $10^6$ cells/ml with an equal amount of an acetate buffer having a pH of 3.0.

A volume of 500 µl of the blood sample was pumped through the fluidic device at a flow rate of 200 µl/minute. Then, 500 µl of an acetate buffer (pH 4.0) was pumped through the fluidic device at a flow rate of 200 µl/minute. Thereafter, the fluidic device was centrifuged to remove any solution remaining in the chamber, and 3.5 µl of a PCR reaction solution was added to the chamber (experimental group).

The 3.5 µl PCR reaction solution was prepared to achieve the following final concentrations of components: 1×PCR buffer, 200 µM of dNTP, 900 nM of each primer, 2.5 mM $MgCl_2$, 1 mg/mL BSA, 5% PEG, 400 nM Taqman™ probe (SEQ ID No: 3: gtactttcag cggggaggaa) and 0.1 units of Taq™ polymerase. The primers had a nucleotide sequence of SEQ ID Nos: 1 and 2, respectively. As a comparative experiment, DNA was isolated from the blood sample including $10^6$ cells/ml and $10^7$ cells/ml, respectively using a QiAamp™ DNA mini kit (manufactured by QIAGEN™), and PCR was performed using the isolated DNA as a template in the same manner described above (comparative experimental group).

The fluidic device including the chamber was installed in a TMC-1000 (manufactured by Samsung Techwin, Co., Ltd., Korea) to permit PCR to be performed in the fluidic device. Then, E. coli cells attached to the nonplanar solid substrate were disrupted by heat using the procedure described in Example 1.

Then, thermal cycling for PCR was performed after the cell disruption process using the thermal cycling conditions described in Example 1.

Figure 3:
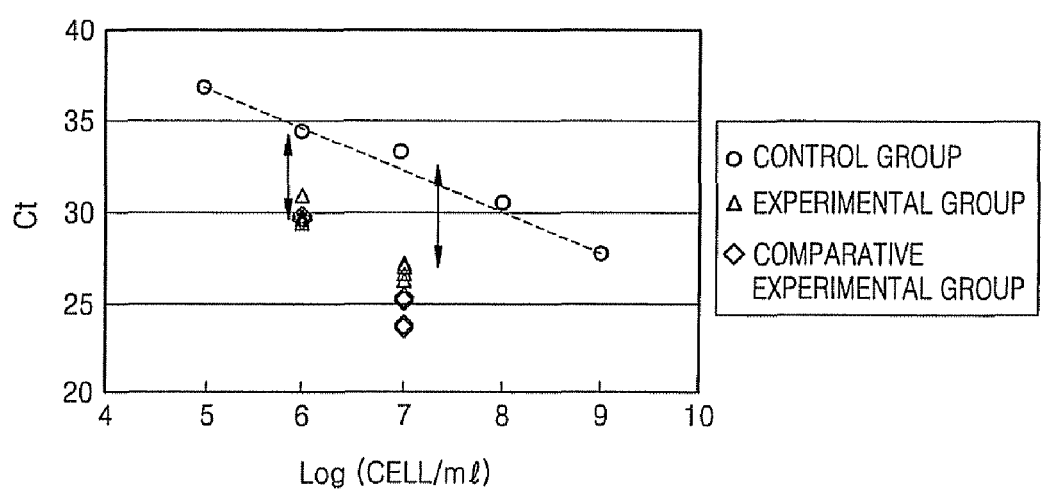
FIG. 3 is a graph showing results of PCR performed on DNA isolated using a nonplanar solid substrate, according to an embodiment of the present invention, or a QIAGEN™ kit, respectively, wherein the PCR results are represented as Ct values.

The concentration of nucleic acid amplified during the PCR process was detected using SYBR™ green. FIG. 3 is a graph showing the results of PCR performed to amplify DNA isolated using a nonplanar solid substrate according to an embodiment of the present invention (experimental group) and DNA isolated using a QIAGEN™ kit (comparative experimental group), respectively, wherein the PCR results are represented as Ct values. A control group PCR experiment was performed by supplying different concentrations of cells, that is, $10^5$ cells/ml, $10^6$ cells/ml, $10^7$ cells/ml, $10^8$ cells/ml, and $10^9$ cells/ml to the chamber without concentrating the cells by attaching the cells to the nonplaner solid substrate (control group). Therefore, according to FIG. 3, the concentration effect of the cells was observed regardless of the concentration of the *E. coli* cells. In FIG. 3, the cell concentration for the experimental group and comparative experimental group at x axis refers to the initial cell concentration prior to the cell concentration process. The Ct values for the experimental group and comparative experiment group are shown as Table 1 below.

TABLE 1

|  | Initial cell concentration (cells/ml) | Ct values |
| --- | --- | --- |
| Experimental group | $10^6$ | 29.64, 31.00, 29.54, 29.70 |
|  | $10^7$ | 27.73, 26.3, 27.13, 26.7 |
| Comparative experimental group | $10^6$ | 29.5, 29.9 |
|  | $10^7$ | 25.9, 23.64, 23.70, 25.61 |

Figure 4:
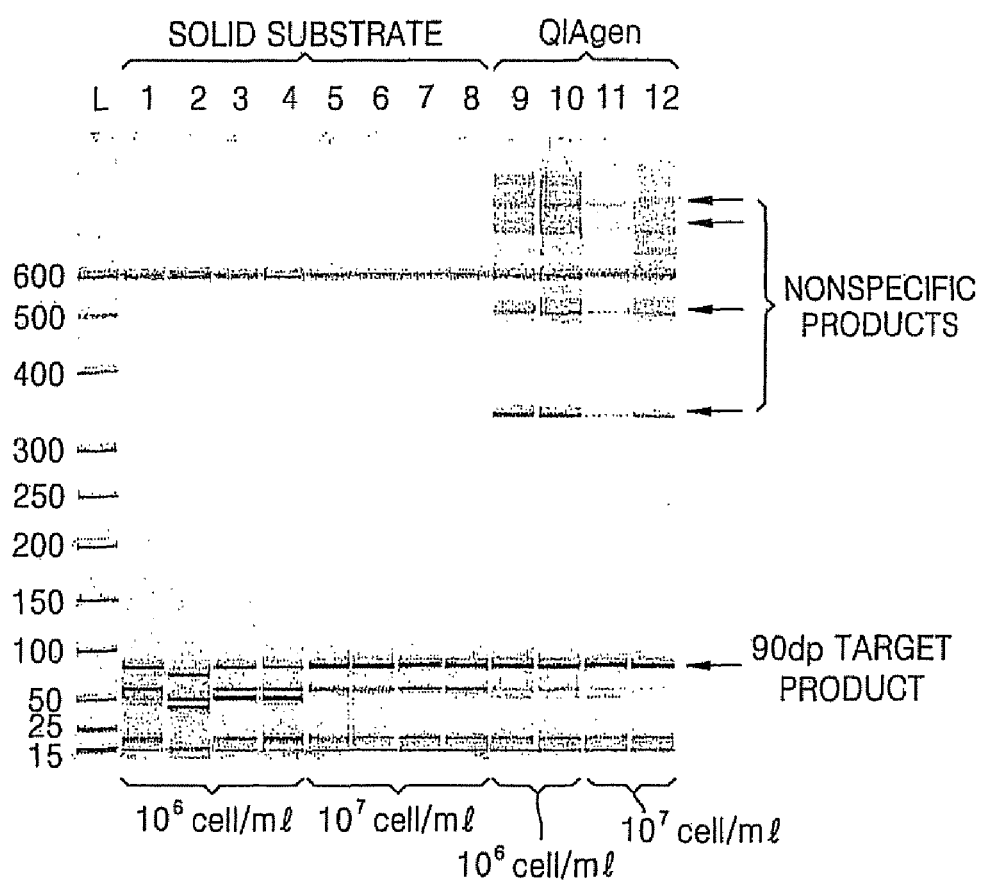
FIG. 4 is a photographic image showing the results of an electrophoretic analysis of PCR products obtained from DNA isolated using a nonplanar solid substrate, according to an embodiment of the present invention, and DNA isolated using a QIAGEN™ kit, respectively.

FIG. 4 is a photographic image of results of an electrophoretic analysis of PCR products obtained from PCR amplifying DNA isolated using a nonplanar solid substrate (lanes 1-8), according to an embodiment of the present invention, and DNA isolated using a QIAGEN™ kit (lanes 9-12), respectively. In FIG. 4, lanes 1-4 refer to results of an electrophoretic analysis of PCR products obtained from PCR amplifying DNA isolated using a nonplanar solid substrate and a sample including *E. coli* having a concentration of $10^6$ cells/ml, which are 4 time repeats of same experiments. Lanes 5-8 refer to results of an electrophoretic analysis of PCR products obtained from PCR amplifying DNA isolated using a nonplanar solid substrate and a sample including *E. coli* having a concentration of $10^7$ cells/ml, which are 4 time repeats of same experiments. Lanes 9-10, and lanes 11-12 refer to results of an electrophoretic analysis of PCR products obtained from PCR amplifying DNA isolated using a QIAGEN™ kit and a sample including *E. coli* having a concentration of $10^6$ cells/ml and $10^7$ cells/ml, respectively, which are 2 time repeats of same experiments, respectively. L refers to a DNA ladder. In FIG. 4, the expected size of target product is 90 bp.

As illustrated in FIG. 4, when a QIAGEN™ kit was used to isolate the template DNA, the PCR amplified nonspecific products. However, when PCR was performed using DNA isolated using the nonplanar solid substrate, the PCR did not amplify the nonspecific products present in the sample amplifying DNA isolated using the QIAGEN™ kit. Therefore, when the method of amplifying nucleic acid from a cell according to an embodiment of the present invention is used, specificity of nucleic acid amplification is high resulting in the amplification of fewer nonspecific PCR products.

Example 4

DNA Amplification Using a Nonplanar Solid Substrate Having a Pillar Structure: Effect of Nonplanar Solid Substrate Surface In the current Example, PCR was performed on a nonplanar solid substrate by including DNA in a fluidic device as described in Example 1.

The pillar array had the dimensions described in Example 1 and its surface was formed of a $SiO_2$ layer. In some pillar arrays tested, the $SiO_2$ layer was coated with OTC or PEIM. 3.5 µl of a PCR reaction solution was supplied to the chamber. The PCR reaction solution was prepared such that the final volume of 3.5 µl included the following components: 1×PCR buffer, 200 µM dNTP, 900 nM of each primer, 2.5 mM $MgCl_2$, 1 mg/mL BSA, 5% PEG, 400 nM of Taqman probe, 1 ng of bacterial genomic DNA and 0.1 units of Taq polymerase. Each of the primers had a nucleotide sequence of SEQ ID Nos: 1 or 2, respectively.

Then the fluidic device including the chamber was installed in a TMC-1000 (manufactured by Samsung Techwin, Co., Ltd., Korea), and thermal cycling for PCR was performed. Conditions of the thermal cycling were as follows: predenaturation at 94° for 10 seconds, 40 cycles of denaturation at 94° for 5 seconds, annealing at 45° for 20 seconds and extension at 72° for 20 seconds.

The concentration of nucleic acid amplified during the PCR process was detected using the Taqman probe. The Ct values of amplified products obtained with each sample are shown in Table 1 below. "SiO2" refers to a nonplanar solid substrate having the pillar array formed of a $SiO_2$ layer. "OTC" refers to a nonplanar solid substrate having the pillar array formed of a $SiO_2$ layer coated with OTC. "PEIM" refers to a nonplanar solid substrate having the pillar array formed of a $SiO_2$ layer coated with PEIM.

TABLE 2

| solid substrate type | Ct value |
| --- | --- |
| SiO2_1 | 17.75 |
| SiO2_2 | 16.68 |
| OTC-1 | 16.79 |
| OTC-2 | 16.22 |
| PEIM_1 | 30.19 |
| PEIM_2 | 33 |

As shown in Table 2, a nonplanar solid substrate having the pillar array formed of a $SiO_2$ and coated with OTC did not affect the Ct value observed in the PCR process. In the case where PCR was preformed using a chamber comprising a nonplanar solid substrate having the pillar array formed of a $SiO_2$ layer coated with PEIM, the PCR failed to efficiently amplify any PCR products. Without being held to theory, it is believed that the PCR was unsuccessful when preformed using a chamber comprising a nonplanar solid substrate having the pillar array formed of a $SiO_2$ layer coated with PEIM because a nonplanar solid substrate coated with PEIM has a positively-charged surface, but, the invention is not limited to such a specific mechanism.

Example 5

Separation of *E. coli* Cells from Blood or Urine, Disruption and Nucleic Acid Amplification from the *E. coli* Cells, Using a Nonplanar Solid Substrate Having a Pillar Structure: Effect of Sample Types In the current example, a blood or urine sample including cells was pumped through a fluidic device as described in Example 1 to attach the cells to the nonplanar solid substrate. Then, the nonplanar solid substrate was washed to remove materials that were not attached thereto. Thereafter, the cells attached to the nonplanar solid substrate were disrupted by heat to obtain cell a lysate, and PCR was performed using DNA from the cell lysate as a template.

The pillar array was as described in Example 1, with the SiO$_2$ layer coated with OTC.

A sample having a pH of 4.8 obtained by mixing blood including *E. coli* (OD$_{600}$=0.01) having a concentration of about 10$^7$ cells/ml or urine including *E. coli* (OD$_{600}$=0.01) having a concentration of about 10$^7$ cells/ml with an equal amount of an acetate buffer having a pH of 3.0 was used in these experiments.

500 µl of the blood or urine sample was pumped through the fluidic device at a flow rate of 200 µl/minute. Then, 500 µl of an acetate buffer (pH 4.0) was pumped through the fluidic device at a flow rate of 200 µl/minute. Thereafter, the fluidic device was centrifuged to remove any solution remaining in the chamber, and 3.5 µl of a PCR reaction solution was added to the chamber.

The 3.5 µl PCR reaction solution was prepared such that the final concentrations of the components were: 1×PCR buffer, 200 µM dNTP, 900 nM of each primer, 2.5 mM MgCl$_2$, 1 mg/mL BSA, 5% PEG, 400 nM Taqman™ probe and 0.1 units of Taq™ polymerase. The primers had a nucleotide sequence of SEQ ID Nos: 1 or 2, respectively.

The fluidic device including the chamber was installed in a TMC-1000 (manufactured by Samsung Techwin, Co., Ltd., Korea) for performance of PCR in the fluidic device. Then, *E. coli* cells were disrupted by heat, as described in Example 1

Then, thermal cycling for PCR was performed after the cell disruption process. Conditions of the thermal cycling were as follows: predenaturation at 94° for 10 seconds, denaturation at 94° for 5 seconds, annealing at 45° for 20 seconds and extension at 72° for 20 seconds. The denaturation, annealing and extension cycle was repeated 40 times.

Figure 5:
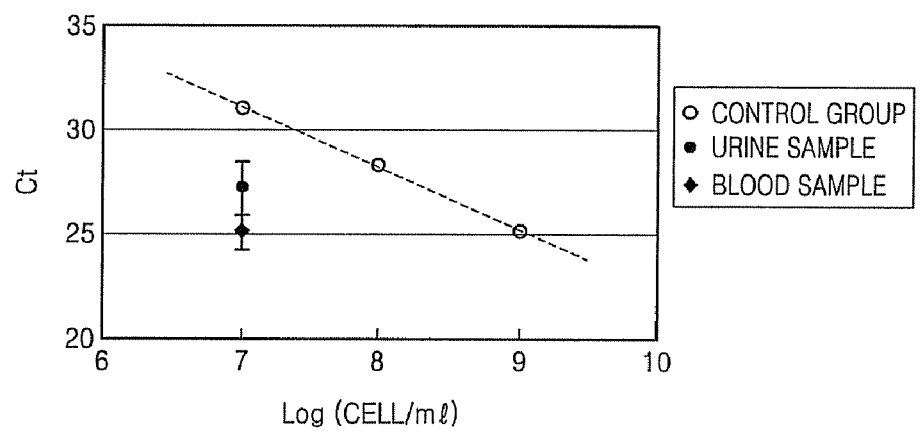
FIG. 5 is a graph showing results of nucleic acid amplification, according to an embodiment of the present invention, in which amplification was performed after *E. coli* in a blood or urine sample was separated from the sample by contacting the *E. coli*-containing sample with a nonplanar solid substrate having a surface that is coated with OTC, followed by cell disruption.

The concentration of nucleic acid amplified during the PCR process was detected using the Taqman™ probe. FIG. 5 is a graph showing the results of nucleic acid amplification performed using template DNA obtained after the *E. coli* was separated from the blood or urine sample by contacting the sample with a nonplanar solid substrate having a surface that is coated with OTC, according to an embodiment of the present invention. In FIG. 5, for the control group, PCR was performed in the same manner as described above except that DNA isolated using a QIAGEN™ DNA mini kit (manufactured by QIAGEN™) was used for PCR. As illustrated in FIG. 5, DNA from cells in the blood or urine sample have a lower Ct value than DNA from cells in the control group. From the results, it can be seen that cells in the blood or urine sample were concentrated by 117 times or 20.9 times, respectively, as compared to the control group. In FIG. 5, the Ct value for the blood sample is lower than that of urine sample. In FIG. 5, the cell concentration for the urine sample and blood sample at x axis refers to the initial cell concentration prior to subsequent cell concentration process.

Example 6

Confirmation of Whether Sodium Polyanethol Sulfonate (SPS) is Bound to a Nonplanar Solid Substrate Having a Pillar Structure In the current example, a solution containing sodium polyanethol sulfonate (SPS) was flowed into a fluidic device comprising a nonplanar solid substrate having pillar arrays formed on a chip having an area of 7.5 mm×15 mm (Chip 1) or a chip having an area of 10 mm×23 mm (Chip 2). Spectroscopic analysis of the solution was performed before and after the solution was passed through the fluidic device, to determine whether SPS was attached to the nonplanar solid substrate.

The configuration of the pillar arrays was as described in Example 1 and the surface of the nonplanar solid substrate having the pillar arrays formed thereon was formed of a SiO$_2$ layer.

A solution comprising a blood culture media solution containing 0.05% SPS was used as the solution including SPS. 500 µl of the solution was pumped through the fluidic device at a flow rate of 200 µl/minute.

Figure 6:
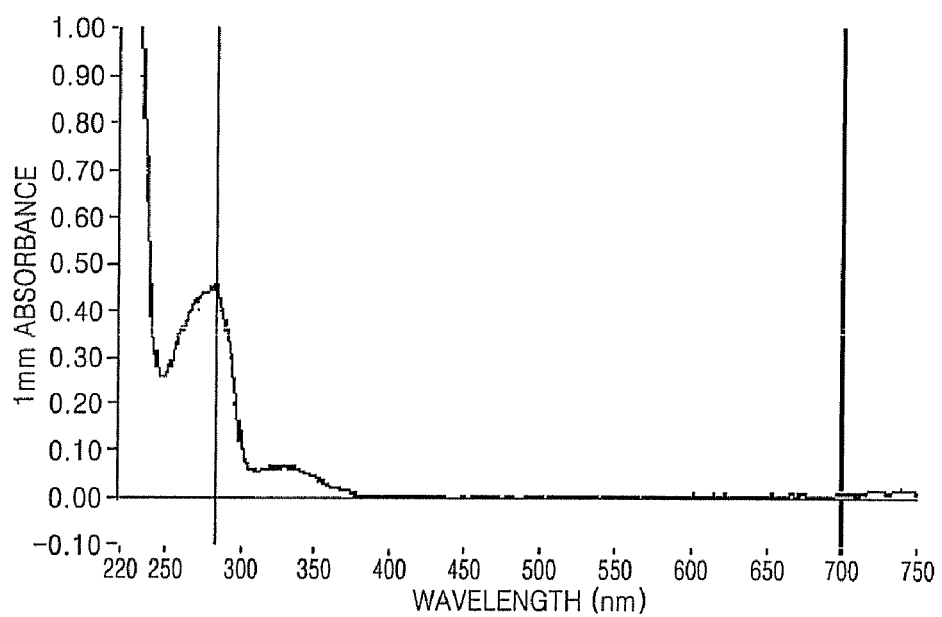
FIGS. 6 and 7 are graphs showing results of spectroscopic analysis of a solution containing SPS before (FIG. 6) and after (FIG. 7) the solution containing SPS is pumped through the fluidic device including a nonplanar solid substrate.
Figure 7:
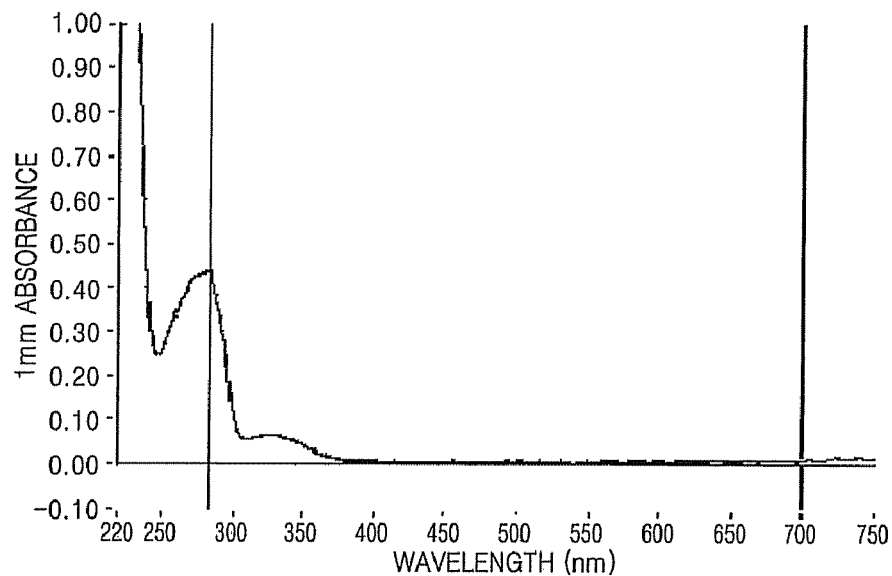

FIGS. 6 and 7 are graphs showing the results of spectroscopic analysis of a solution containing SPS in the case of before (FIG. 6) and after (FIG. 7) the solution containing SPS is pumped through the fluidic device, according to an embodiment of the present invention. As illustrated in FIGS. 6 and 7 for chip 1, the spectroscopic curve obtained before the solution was passed through the fluidic device was almost the same as the spectroscopic curve obtained after the solution was passed through the fluidic device. The result indicates that the SPS is not attached to on the nonplanar solid substrate used in the current example. Similar results were observed for chips 1 and 2.

Example 7

Amplification of Nucleic Acid from a Blood Culture Using a Nonplanar Solid Substrate Having a Pillar Structure: Effect of SPS In the current example, a blood culture containing *E. coli* and SPS was pumped through a fluidic device as described in Example 1 to attach the *E. coli* cells to the nonplanar solid substrate. Then, the nonplanar solid substrate was washed to remove materials that were not attached thereto. Thereafter, the cells attached to the solid substrate were disrupted by heat to obtain cell lysate, and PCR was performed using DNA from the cell lysate as a template.

The pillar array was as described in Example 1.

A blood culture sample having a pH of 4.7 was obtained by mixing a blood culture including *E. coli* of 0.01 OD$_{600}$ and SPS with 100 mM sodium acetate buffer having a pH of 3.0 in a ratio of 1:1. The blood culture was prepared by adding *E. coli* having a certain concentration to BHI medium including 0.05% SPS and 10% blood, and is very similar to a blood culture. For the experiment, the *E. coli* cells were added to the BHI medium in a predetermined concentration. A control group was prepared by performing the same processes as described above, except that a general blood culture excluding SPS was used. The general blood culture used a BHI medium containing *E. coli* cell but did not include SPS or blood.

500 µl of the blood culture sample was pumped through the fluidic device at a flow rate of 200 µl/minute. Then, 500 µl of an acetate buffer (pH 4.0) was pumped through the fluidic device at a flow rate of 500 µl/minute. Thereafter, the fluidic device was centrifuged to remove any solution remaining in the chamber, and 3.5 µl of a PCR reaction solution was added to the chamber. The PCR reaction solution was prepared by mixing components to achieve the following concentrations in a total volume of 3.5 µl: 1×PCR buffer, 200 µM dNTP, 200 nM of each primer, 2.5 mM MgCl$_2$, 1 mg BSA, 5% PEG, 400 nM Taqman probe (SEQ ID NO: 3) and 0.1 units of Taq polymerase to reach. The primers had a nucleotide sequence of SEQ ID Nos: 1 or 2, respectively.

The fluidic device including the chamber was installed in a TMC-1000 (manufactured by Samsung Techwin, Co., Ltd., Korea) for PCR. Then, *E. coli* cells were disrupted by heat, as described in Example 1.

Then, thermal cycling for PCR was performed after the cell disruption process. Conditions of the thermal cycling were as follows: predenaturation at 94° for 10 seconds, denaturation at 94° for 5 seconds, annealing at 45° for 20 seconds and extension at 72° for 20 seconds. The denaturation, annealing and extension cycle was repeated 40 times.

Figure 8:
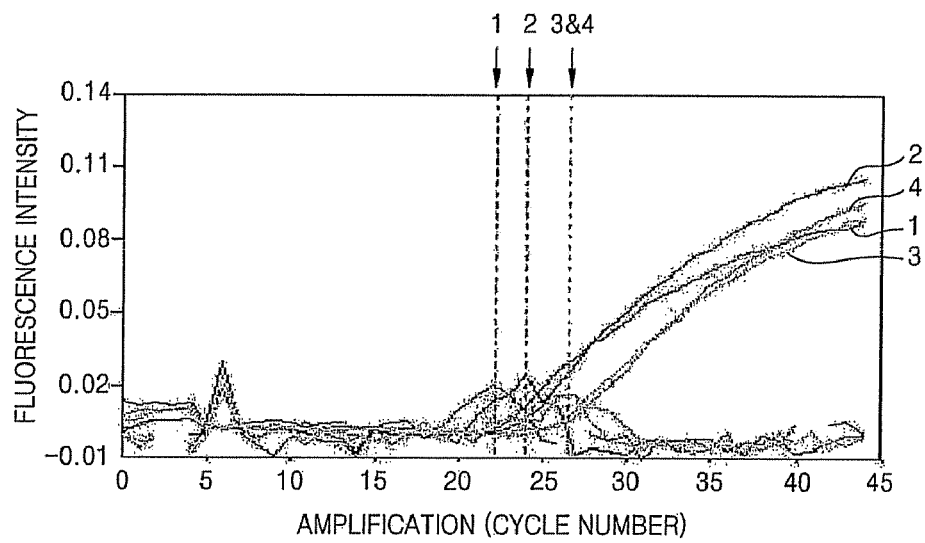
FIG. 8 is a graph illustrating the results of a real-time PCR performed on *E. coli* cells separated from a blood culture including SPS and a blood culture excluding SPS, using a fluidic device comprising a nonplanar solid substrate, wherein the *E. coli* cells were disrupted, and the DNA from the disrupted cells was used as a template.

The concentration of nucleic acid amplified during the PCR process was detected using a Taqman™ probe. FIG. 8 is a graph that illustrates the results of real-time PCR amplifying DNA obtained by separating *E. coli* cells from a blood culture including SPS, or DNA obtained by separating *E. coli* cells from a blood culture excluding SPS using a fluidic device including a nonplanar solid substrate and then disrupting the *E. coli* cells, and using DNA from the disrupted cells as a template. In FIG. 8, curves 1 and 2 refer to real-time PCR products curves for DNA obtained by separating *E. coli* cells from a blood culture excluding SPS, which are for the 2 time repeats experiments for the same conditions, and curves 3 and 4 refer to real-time PCR products curves for DNA obtained by separating *E. coli* cells from a blood culture including SPS, which are for the 2 time repeats experiments for the same conditions. The vertical Ct lines 1 and 2, 3 and 4 correspond to curves 1 and 2, and 3 and 4, respectively.

Figure 9:
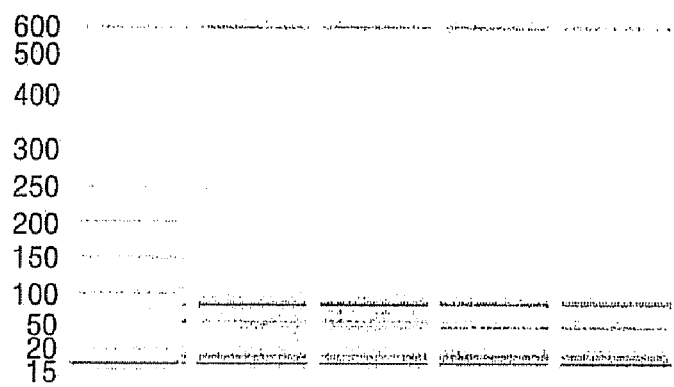
FIG. 9 is an image of the results of an electrophoretic analysis of PCR performed on *E. coli* cells separated from a blood culture including SPS and a blood culture excluding SPS, using a fluidic device including a nonplanar solid substrate, wherein the *E. coli* cells were disrupted, and the DNA from the disrupted cells was used as a template.

FIG. 9 is a photographic image of the results of an electrophoretic analysis of PCR amplifying DNA obtained by separating *E. coli* cells from a blood culture including SPS or DNA obtained by separating *E. coli* cells from a blood culture excluding SPS using a fluidic device including a nonplanar solid substrate and then disrupting the *E. coli* cells, and using DNA from the disrupted cells as a template. In FIG. 9, lane 1 refers to a DNA ladder, lanes 2 and 3 refer to a blood culture excluding SPS and lanes 3 and 4 refer to a blood culture including SPS. In FIG. 9, the expected size of target product is 90 bp.

As illustrated in FIGS. 8 and 9, PCR amplification of DNA obtained from *E. coli* cells from a blood culture including SPS is as efficient as amplification of DNA obtained from *E. coli* cells from a blood culture excluding SPS. Thus, even when the blood culture containing SPS was used as a sample, target nucleic acid was amplified with a Ct similar to the Ct of target nucleic acid amplified when the blood culture excluding SPS was used as a sample. The results show that in the method of amplifying nucleic acid from a cell according to an embodiment of the present invention, target nucleic acid can be amplified efficiently from a sample containing SPS, without additional steps to remove the SPS.

Example 8

Amplification of Nucleic Acid from a Sample Including SPS Using a Nonplanar Solid Substrate Having a Pillar Structure: Effect of SPS In the current example, a blood culture including *E. coli* and SPS was pumped through a fluidic device as described in Example 1m to attach the *E. coli* cells to the nonplanar solid substrate. Then, the nonplanar solid substrate was washed to remove materials that were not attached thereto. Thereafter, the cells attached to the nonplanar solid substrate were disrupted with an alkali solution and heat to obtain cell lysate. PCR was performed using DNA from the cell lysate as a template.

A blood culture sample having a pH of 4.7 was obtained by mixing a blood culture including *E. coli* of 0.01 $OD_{600}$ and SPS with 100 mM sodium acetate buffer having a pH of 3.0 in a ratio of 1:1. The blood culture was prepared by adding *E. coli* to BHI medium including 0.05% SPS and 10% blood, and is very similar to a blood culture. For this experiment, the *E. coli* cell was added to the BHI medium in a predetermined concentration. A control group was prepared by performing the same processes as described above, except that a general blood culture excluding SPS was used. The general blood culture was a BHI medium containing *E. coli* cell but which did not include SPS and blood.

500 µl of the blood culture sample was pumped through the fluidic device at a flow rate of 200 µl/minute. Then, 500 µl of an acetate buffer (pH 4.0) was pumped through the fluidic device at a flow rate of 500 µl/minute. Thereafter, the fluidic device was centrifuged to remove any solution remaining in the chamber, and 0.01 N NaOH solution was added to the chamber. Then, the fluidic device was left to sit at 95° C. for 5 minutes to disrupt the *E. coli* cells. The fluidic device was centrifuged again to obtain 2 ml of *E. coli* cell lysate. As Comparative Experiments 3 and 4, DNA was isolated from *E. coli* using a QIAGEN™ mini kit from the medium including 0.05% SPS and 10% blood and the medium excluding 0.05% SPS and 10% blood to finally obtain 50 µl of a DNA solution. In addition, as Comparative Experiments 1 and 2, a 5 ng/µl DNA solution and a solution including 0.05% SPS and 5 ng/µl DNA were used. As Comparative Experiments 5 and 6, PCR was performed using a medium including 0.05% SPS and 10% blood and a medium excluding 0.05% SPS and 10% blood, without isolation of nucleic acid from either sample prior to PCR.

For PCR, a PCR reaction solution was added to a PCT tube. The 50 µl PCR reaction solution was prepared by mixing components to achieve the following final concentrations: 1×PCR buffer, 200 µM of dNTP, 200 nM of each primer, 2.5 mM of $MgCl_2$, 1 µl of each template and 2.5 units of Taq polymerase. The primers had a nucleotide sequence of SEQ ID Nos: 1 and 2, respectively.

Thermal cycling for PCR was performed. Conditions of the thermal cycling were as follows: predenaturation at 95° C. for 1 minute, denaturation at 95° C. for 5 seconds, annealing at 62° C. for 13 seconds and extension at 72° C. for 15 seconds. The denaturation, annealing and extension cycles were repeated 25 times.

Figure 10:
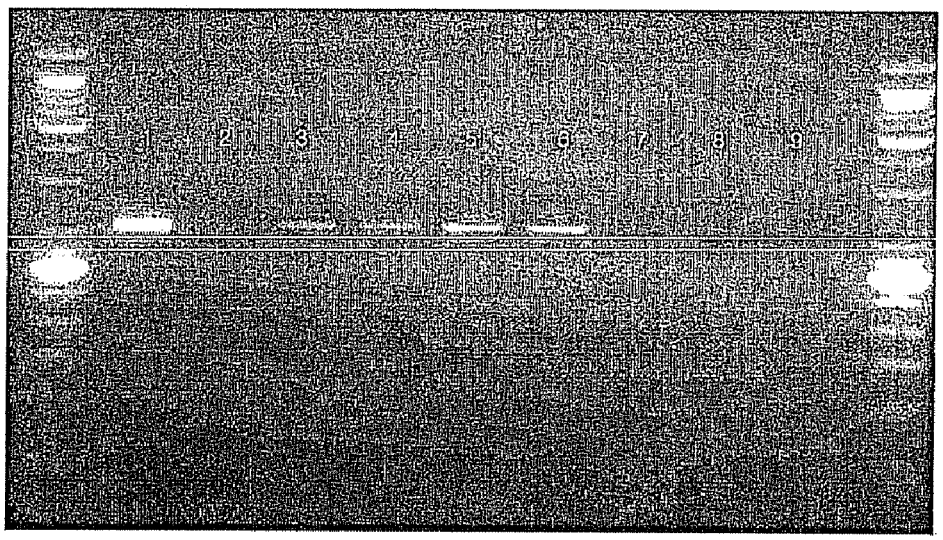
FIG. 10 is a photographic image of the results of an electrophoretic analysis of PCR products obtained using various DNA templates that include SPS or exclude SPS.

FIG. 10 is a photographic image of the results of an electrophoretic analysis of PCR using various DNA templates obtained from samples that include SPS or exclude SPS. In FIG. 10, Lanes 1 through 9 represent electrophoresis results for the following DNA samples:

Lane 1: DNA (Comparative Experiment 1),

Lane 2: DNA+0.05% of SPS (Comparative Experiment 2),

Lane 3: a sample in which nucleic acid is isolated from a culture medium including 0.05% of SPS and 10% of blood and *E. coli* of 0.005 OD600 using a QIAGEN™ mini kit, (Comparative Example 3)

Lane 4: a sample in which nucleic acid is isolated from a culture medium comprising and *E. coli* of 0.005 OD600 and excluding 0.05% of SPS and 10% of blood using a QIAGEN™ mini kit (Comparative Example 4), Lane 5: a sample in which a culture medium including 0.05% of SPS and 10% of blood and *E. coli* of 0.005 OD600 is passed through a fluidic device including a nonplanar solid substrate according to an embodiment of the present invention, E. coli cells bound to the solid substrate disrupted, and then nucleic acid is eluted from the solid substrate (Experiment 1), Lane 6: a sample in which a culture medium comprising and E. coli of 0.005 OD600 and excluding 0.05% of SPS and 10% of blood is passed through a fluidic device including a solid substrate according to an embodiment of the present invention, E. coli cells bound to the solid substrate disrupted, and then nucleic acid is eluted from the solid substrate (Control Experiment), Lane 7: a sample in which a culture medium including 0.05% of SPS and 10% of blood and E. coli of 0.005 OD600 is directly used for PCR (Comparative Experiment 5), Lane 8: a sample in which a culture medium excluding 0.05% of SPS and 10% of blood and E. coli of 0.005 OD600 is directly used for PCR (Comparative Experiment 6), and Lane 9: a negative control group which does not include a target DNA.

As illustrated in FIG. 10, it can be seen that SPS is a PCR inhibitor (Lane 2). However, PCR amplification of DNA obtained from E. coli cells separated from a blood culture including SPS, according an embodiment of the current invention, is efficiently performed (lanes 5 and 6). Specifically, it was confirmed that the present method (lanes 5 and 6)_was more efficient than that of conventional method, that is, a method using a QIAGEN™ mini kit (lanes 3 and 4). Lanes 7 and 8 show that culture medium with or without SPS inhibits PCR. From the results, it is confirmed that in the process of separating E. coli cells using the nonplanar solid substrate according to an embodiment of the present invention, SPS is not attached to the nonplanar solid substrate, and is thereby removed. Thus, the results show that no additional steps to separately remove the SPS from the sample are necessary.

In the method of amplifying nucleic acid from a cell according to the present invention, cell separation, cell disruption and nucleic acid amplification are performed in a single vessel, and thus nucleic acid can be amplified conveniently, quickly and with high sensitivity. Also, these processes can be easily automated. In addition, since a cell can be contacted with a nonplanar solid substrate at a high flow rate in order to attach the cell to the nonplanar solid substrate, an initial sample containing a large amount of cells can be used.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of amplifying nucleic acid from a cell comprising:
   contacting a sample comprising a cell and polyanethole sulfonate with a nonplanar solid substrate in a liquid medium having a pH in a range of 3.0-6.0 to attach the cell to the nonplanar solid substrate,
   wherein the nonplanar solid substrate is hydrophobic and has a water contact angle of 70° to 95° or the nonplanar solid substrate has at least one amine-based functional group at its surface prepared by coating the nonplanar solid substrate with polyethyleneiminetrimethoxysilane (PEIM);
   washing the nonplanar solid substrate to remove materials that are not attached thereto; and
   performing a polymerase chain reaction (PCR) using the cell attached to the nonplanar solid substrate as a template sample to amplify nucleic acid from the cell,
   wherein the contacting, washing and performing the PCR are performed in a single vessel and the cell is a microorganism cell.

2. The method of claim 1, wherein the sample is blood, blood culture, urine or saliva.

3. The method of claim 1, wherein the cell is a bacterial cell, a fungus, or a virus.

4. The method of claim 1, wherein the sample is diluted in the liquid medium, which is a phosphate buffer or an acetate buffer.

5. The method of claim 4, wherein the sample is diluted in a ratio of 1:1 to 1:10.

6. The method of claim 5, wherein the liquid medium has a salt concentration of 10 mM to 500 mM.

7. The method of claim 6, wherein the sample has a salt concentration of 50-300 mM.

8. The method of claim 1, wherein the nonplanar solid substrate is a solid substrate comprising a surface with a plurality of pillars, a bead-shaped solid substrate, or a sieve-shaped solid substrate having a plurality of pores.

9. The method of claim 8, wherein the pillars have an aspect ratio of 1:1-20:1, wherein the aspect ratio refers to a ratio of the cross-sectional diameter of a pillar to the height of a pillar.

10. The method of claim 8, the plurality of pillars comprises a pillar structure with a ratio of a height of the pillars to a distance between adjacent pillars in the range of 1:1 to 25:1.

11. The method of claim 8, wherein the plurality of pillars comprises a pillar structure and a distance between adjacent pillars is in the range of 5 μm to 100 μm.

12. The method of claim 1, wherein the hydrophobic nonplanar solid substrate is obtained by coating octadecyldimethyl(3-trimethoxysilyl propyl)ammonium (OTC) or tridecafluorotetrahydrooctyltrimethoxysilane (DFS) on a surface of the nonplanar solid substrate.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
tgtatgaaga aggcttcg                                                  18

<210> SEQ ID NO 2
<211> LENGTH: 19
<212> TYPE: DNA
<213> ORGANISM: Artificial
<220> FEATURE:

```
<223> OTHER INFORMATION: primer

<400> SEQUENCE: 2
aaaggtatta actttactc                                            19

<210> SEQ ID NO 3
<211> LENGTH: 20
<212> TYPE: DNA
<213> ORGANISM: Artificial
<220> FEATURE:
<223> OTHER INFORMATION: Probe

<400> SEQUENCE: 3
gtactttcag cggggaggaa                                           20
```